US00PP31542P2

(12) United States Plant Patent
Merz

(10) Patent No.: US PP31,542 P2
(45) Date of Patent: Mar. 10, 2020

(54) ***CAREX* PLANT NAMED 'MMCREAM'**

(50) Latin Name: *Carex morrowii*
Varietal Denomination: MMCream

(71) Applicant: Michael Merz, Offenbach am Main (DE)

(72) Inventor: Michael Merz, Offenbach am Main (DE)

( * ) Notice: Subject to any disclaimer, the term of this patent is extended or adjusted under 35 U.S.C. 154(b) by 0 days.

(21) Appl. No.: 16/350,206

(22) Filed: Oct. 12, 2018

(51) Int. Cl.
*A01H 5/12* (2018.01)

(52) U.S. Cl.
USPC ..... Plt./384

(58) Field of Classification Search
USPC ..... Plt./384
CPC ..... A01H 5/12; A01H 6/00
See application file for complete search history.

*Primary Examiner* — Keith O. Robinson

(57) ABSTRACT

A new cultivar of *Carex* plant named 'MMCream' that is characterized by variegated leaves with green centers and cream-white margins, wide leaves and good stress resistance to frost and drought.

1 Drawing Sheet

Botanical classification: *Carex morrowii.*
Variety denomination: 'MMCream'.

BACKGROUND OF THE INVENTION

The present invention relates to a new and distinct cultivar of *Carex* plant botanically known as *Carex morrowii* and hereinafter referred to by the cultivar name 'MMCream'.

The new *Carex* is a naturally-occurring whole plant mutation of *Carex morrowii* 'Vanice' (not patented). The new *Carex* was discovered and selected by the Inventor as a single plant from within a population of plants of the parent in a controlled greenhouse environment in a cultivated area of Offenbach, Germany in 2016.

Asexual reproduction of the new cultivar 'MMCream' first occurred by division in 2016 in Offenbach, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Carex* cultivar 'MMCream'. These traits in combination distinguish 'MMCream' as a new and distinct cultivar apart from other existing known varieties of *Carex*.

1. *Carex* 'MMCream' exhibits variegated leaves with green centers and cream-white margins.
2. *Carex* 'MMCream' exhibits wide leaves.
3. *Carex* 'MMCream' exhibits good stress resistance to frost and drought.

The closest comparison cultivars are *Carex* 'Ice Ballet' (U.S. Plant Pat. No. 20,228) and the parent plant 'Vanice'. 'MMCream' is distinguishable from 'Ice Ballet' by the following characteristics:

1. *Carex* 'MMCream' exhibits variegated leaves with green centers and cream-white margins. In contrast, the leaves of 'Ice Ballet' have darker green centers and lighter cream-white margins.
2. *Carex* 'MMCream' exhibits wider leaves than the leaves of 'Ice Ballet'.

3. *Carex* 'MMCream' exhibits better stress resistance to frost and drought than 'Ice Ballet'.

'MMCream' is distinguishable from the parent plant 'Vanice' by the following characteristics:

1. *Carex* 'MMCream' exhibits variegated leaves with green centers and cream-white margins. In contrast, the leaves of 'Vanice' have narrower cream-white margins.
2. *Carex* 'MMCream' exhibits wider leaves than the leaves of 'Vanice'.
3. *Carex* 'MMCream' exhibits better stress resistance to frost and drought than 'Vanice'.

BRIEF DESCRIPTION OF THE DRAWING

The accompanying photograph illustrates the distinguishing traits of *Carex* 'MMCream'. The plant in the photograph shows an overall view of an 18 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Carex* cultivar named 'MMCream'. Data was collected in Mainz, Germany from 18 month old greenhouse grown plants in 20 cm. diameter containers. The time of year was Spring and the temperature averaged 17 degrees Centigrade during the day and 10 degrees Centigrade at night. No growth retardants were used. Color determinations are in accordance with The Royal Horticultural Society Colour Chart 2007 edition, except where general color terms of ordinary dictionary significance are used. The growing requirements are similar to the species. 'MMCream' has not been tested under all possible conditions and phenotypic differences may be observed with variations in environmental, climatic, and cultural conditions, however, without any variance in genotype.

Botanical classification: *Carex morrowii* 'MMCream'.
Annual or perennial: Perennial.

Parentage: 'MMCream' is a naturally occurring whole plant mutation of *Carex* 'Vance'.
Vigor: Moderate.
Growth habit: Clumping habit with curved foliage.
Plant shape: Upright with outwardly arching foliage.
Suitable container size: 20 cm. and larger.
Height: Average 29.0 cm. in height.
Diameter: Average 73.0 cm. in diameter.
Low temperature tolerance: −20° Centigrade.
High temperature tolerance: 35° Centigrade.
Propagation: Division.
Time to initiate roots: About 20 days.
Time to produce a rooted young plant: 12 weeks.
Root system: Short, stout rhizomes with dense fibrous roots.
Root color: 145D.
Branching: No stems, shoots arise from rhizomes.
Foliage:
- *Number of shoots per plant.*—Average 18.
- *Number of leaves per shoot.*—Average 10.
- *Leaf shape.*—Linear.
- *Leaf division.*—Simple.
- *Leaf apex.*—Attenuate.
- *Leaf base.*—Sheathed to rhizome.
- *Leaf aspect.*—Leaves initially emerge upright, then arch outward.
- *Leaf dimensions.*—Average 39.9 cm. in length and 1.3 cm. in width.
- *Texture.*—Glabrous on both surfaces.
- *Pubescence.*—Absent on both surfaces.
- *Leaf margin.*—Entire.
- *Venation pattern.*—Parallel.
- *Young leaf color* (*upper surface*).—137B, margins 11B.
- *Young leaf color* (*lower surface*).—137C, margins 11C.
- *Mature leaf color* (*upper surface*).—137A, margins 11B.
- *Mature leaf color* (*lower surface*).—137B, margins 11B.
- *Vein color* (*both surfaces*).—Matches leaf color.
- *Durability of foliage to stress.*—High.

Flower:
- *Inflorescence arrangement.*—Terminal racemes, male and female flowers on separate spikelets.
- *Flowering habit.*—Free flowering with about 34 inflorescences per plant.
- *Inflorescence dimensions.*—Average 22.4 cm. in height and 1.5 cm. in width.
- *Quantity of flowers per inflorescence.*—Average 200.
- *Natural flowering season.*—March to April in Germany.
- *Fragrance.*—None.
- *Flower longevity.*—About 10 days.
- *Bud dimensions.*—5 mm. in length and 2 mm. in diameter.
- *Bud shape.*—Oblong.
- *Bud color.*—198B.
- *Staminate spikelets.*—Narrow ovate in shape, dimensions: Average of 3.2 mm. in diameter and 10.1 mm. in length.
- *Male flower description.*—1 glume and 1 lemma, surfaces smooth, lanceolate in shape, 4.6 mm. in length and 0.5 mm. in width, color N199B.
- *Pistillate spikelets.*—Narrow ovate in shape, dimensions: Average of 2.6 mm. in diameter and 7.3 mm. in length.
- *Female flower description.*—1 glume and 1 lemma, surfaces smooth, lanceolate in shape, 3.4 mm. in length and 0.5 mm. in width, color N199B.
- *Persistent or self-cleaning.*—Persistent.

Peduncle:
- *Peduncle dimensions.*—21.0 cm. in length and 4.4 mm. in diameter.
- *Peduncle angle.*—0 to 15 degrees.
- *Peduncle strength.*—Strong.
- *Peduncle color.*—144B.

Reproductive organs:
- *Number of stamens per flower.*—3.
- *Anther length.*—1.0 mm.
- *Anther shape.*—Ovoid.
- *Anther color.*—165B.
- *Pollen amount.*—Low.
- *Pollen color.*—164C.
- *Number of pistils per flower.*—1.
- *Pistil length.*—1.1 mm.
- *Style length.*—About 1 mm.
- *Style color.*—145A.
- *Stigma shape.*—Fimbriate.
- *Stigma color.*—144A.
- *Ovary color.*—143 C.

Fruit and seed: Fruit and seed production has not been observed to date.
Disease and pest resistance: Disease and pest resistance has not been observed to date.

The invention claimed is:

1. A new and distinct variety of *Carex* plant named 'MMCream' as described and illustrated.

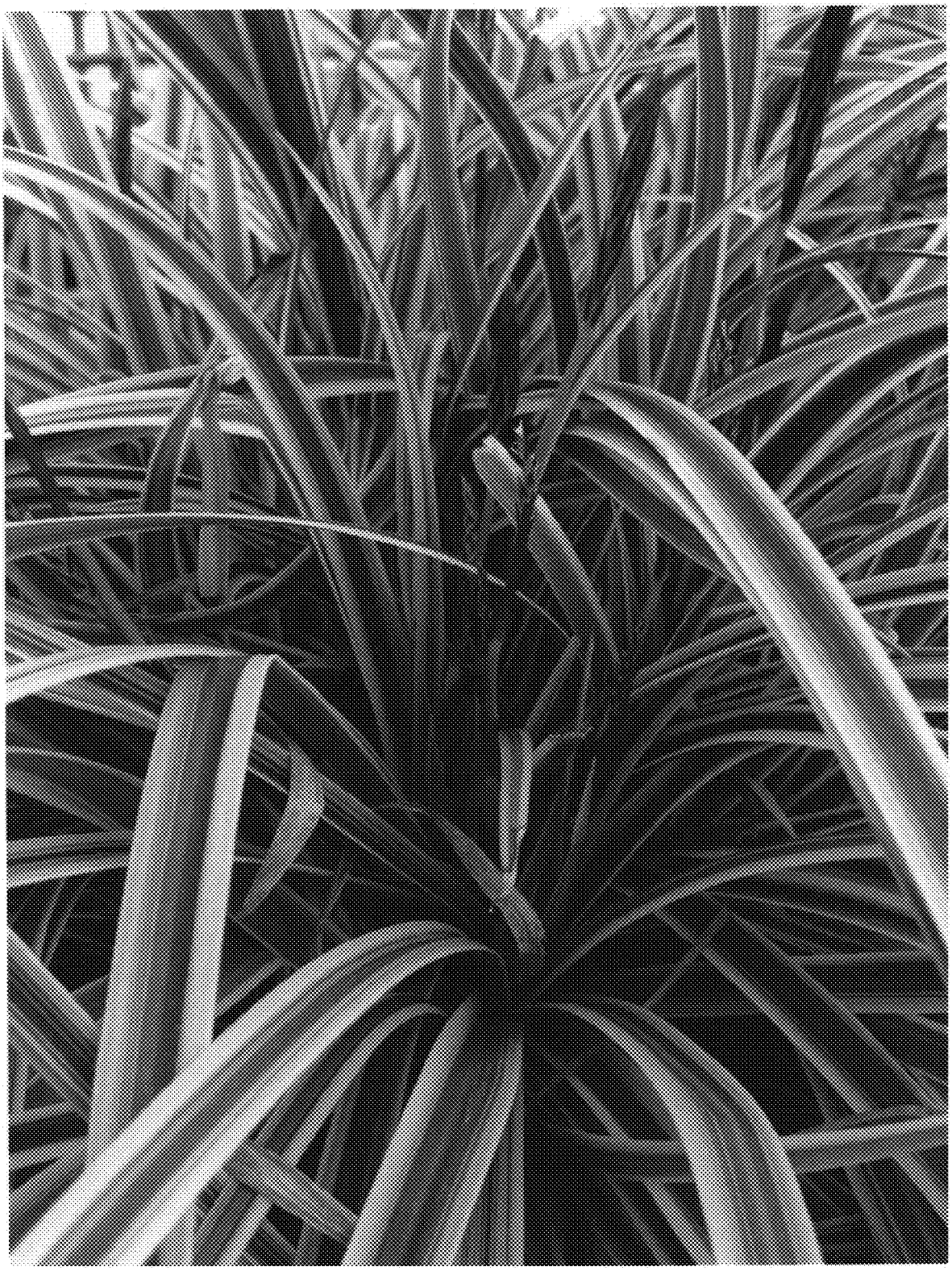

* * * * *